United States Patent [19]

Ikura et al.

[11] Patent Number: 4,777,033

[45] Date of Patent: Oct. 11, 1988

[54] ORAL SUSTAINED RELEASE PHARMACEUTICAL PREPARATION

[75] Inventors: Hiroshi Ikura; Yoshiki Suzuki; Tsuneji Nagai, all of Tokyo; Yoshiharu Machida, Kanagawa, all of Japan

[73] Assignee: Teijin Limited, Osaka, Japan

[21] Appl. No.: 872,996

[22] Filed: Jun. 11, 1986

[30] Foreign Application Priority Data

Jun. 11, 1985 [JP] Japan .................. 60-125139
Jun. 12, 1985 [JP] Japan .................. 60-126337

[51] Int. Cl.$^4$ .................. A61K 9/46; A61K 9/22; A61K 9/26
[52] U.S. Cl. .................. 424/44; 424/81; 424/487; 424/488
[58] Field of Search .................. 424/44, 435, 81, 487, 424/488

[56] References Cited

U.S. PATENT DOCUMENTS

| | | | |
|---|---|---|---|
| 4,059,686 | 11/1977 | Tanaka et al. | 424/435 |
| 4,226,848 | 10/1980 | Nagai et al. | 424/19 |
| 4,292,299 | 9/1981 | Suzuki et al. | 424/435 |
| 4,414,198 | 11/1983 | Michaelson | 424/44 |
| 4,503,031 | 3/1985 | Glassman | 424/44 |
| 4,517,173 | 5/1985 | Kizawa et al. | 424/435 |
| 4,569,837 | 2/1986 | Suzuki et al. | 424/435 |
| 4,572,832 | 2/1986 | Kigasawa et al. | 424/435 |
| 4,680,323 | 7/1987 | Lowey | 424/435 |
| 4,684,516 | 8/1987 | Bhutani | 424/469 |

FOREIGN PATENT DOCUMENTS 0142877  10/1984  European Pat. Off. .

OTHER PUBLICATIONS

Chemical Abstracts, vol. 87, No. 26, Dec. 26, 1977, p. 291, Ref. No. 206530c.

Primary Examiner—Shep K. Rose
Attorney, Agent, or Firm—Sughrue, Mion, Zinn, Macpeak & Seas

[57] ABSTRACT

This invention is concerned with an oral sustained release pharmaceutical preparation which is prepared as a pharmaceutical preparation comprising lower alkyl ether of cellulose, polyacrylic acid or its pharmaceutically acceptable salt, and active drugs, or a pharmaceutical preparation comprising lower alkyl ether of cellulose, polyacrylic acid or its pharmaceutically acceptable salt, and active drugs together with a foaming agent, so that it may release the active drugs by such slow degrees in the stomach or the intestinal tract as to make it possible to provide an adequate supply of active drugs in enough concentration to display their therapeutic value for many hours.

8 Claims, No Drawings

ORAL SUSTAINED RELEASE PHARMACEUTICAL PREPARATION

BACKGROUND OF THE INVENTION

1. Field of the Invention

This invention relates to an oral sustained release pharmaceutical preparation. More particularly, this invention is concerned with an oral sustained release pharmaceutical preparation which is prepared as a pharmaceutical preparation comprising lower alkyl ether of cellulose, polyacrylic acid or its pharmaceutically acceptable salt, and active drugs, or a pharmaceutical preparation comprising lower alkyl ether of cellulose, polyacrylic acid or its pharmaceutically acceptable salt, and active drugs together with a foaming agent, so that it may release the active drugs by such slow degrees in the stomach or the intestinal tract as to make it possible to provide an adequate supply of active drugs in enough concentration to display their therapeutic value for many hours.

2. Description of the Related Art

Various proposals have hitherto been made as to so-called sustained release pharmaceutical preparations which are made to sustain the release of the active drugs from the pharmaceutical preparations so that the efficacy of the active drugs may be maintained for many hours.

For instance, Japanese patent publication No. 13092/'62 gives a description of a sustained release pharmaceutical preparation of oral type comprising an active drug and slight soluble acidic carboxyvinyl polymer and Japanese patent publication No. 17324/'67 carries a description of a granule and a tablet which comprise a mixture of such a hydrophilic resin as polyvinyl alcohol and polyacrylic acid and a drug and display the sustained efficacy in the stomach or the intestinal tract. All of these pharmaceutical preparations are made to hold and display the sustained curative power of their active drugs in the stomach or the intestinal tract. There is, however, a probability that, granting it to be true that these sustained release pharmaceutical preparations have the property of releasing the drugs from the preparations continuously for many hours, the preparation themselves pass the site of absorption or action for the drug before the drug is released from the preparation in the body. In such a case, this most advantageous property of the preparation can not be utilized.

Another attempt is also proposed to prolong the residence time of the preparation in the stomach while allowing the preparation to release the drug in the stomach for a long time, thus keeping the effective blood concentration for many hours.

Examples of this sort might be quoted from Japanese Laid-Open patent publication No. 61323/'74 which describes a preparation comprising a core drug coated with a polymer film which has a property of swelling in gastric juice to prevent the preparation from passing through the pylorus because of its increased mechanical bulkiness, thus prolonging its residence time in the stomach; followed up by another patent, Japanese Laid-Open patent publication No. 115910/'76, which contains a description of a preparation which is designed to release the drug through a hydrogel while being made to float in gastric juice by use of a large amount of fatty substance of low specific gravity.

Though these pharmaceutical preparations mentioned above are intended to release the active drugs in the stomach gradually, they involve a good possibility of allowing themselves to move on to the intestinal tract before the release of the drugs is not completed due to such physiological factors as meal, stress, condition of a disease or external causes.

Japanese Laid-Open patent publication No. 121418/'75 describes a pharmaceutical preparation which consists of a hollow material such as foamed polystyrol, hard gelatin capsule, and expanded grain, having a coating formed thereupon and another coating of the drug applied thereon, to make them float and stay in gastric juice. The preparations of this type have a disadvantage of requiring a complicated producing process.

Japanese Laid-Open patent publication No. 76418/'77 gives a description of a pharmaceutical preparation which is coated with a foaming agent mainly comprising bicarbonate by use of a coating material containing the drug, or is coated with a mixture of a foaming agent and the drug by use of an ordinary plain coating material so that the preparation may float in gastric juice while slowly releasing the drug; however, the preparation of this type has a demerit of having not enough sustained release effect.

On the other hand, Japanese Laid-Open patent publication No. 41320/'79 and Japanese Laid-Open patent publication No. 118414/'80 disclose a sustained release pharmaceutical preparation of oral mucosal adhesion type which comprises lower alkyl ether of cellulose, polyacrylic acid or its pharmaceutically acceptable salt, and drug. This susteined release pharmaceutical preparation has its site of application mainly in the oral cavity and no investigation has yet been made as to its oral administration use.

SUMMARY OF THE INVENTION

It is therefore an object of this invention to provide an oral sustained release pharmaceutical preparation which releases the active drug gradually in the stomach or the intestinal tract after it is orally administered so that the active drug might be supplied in sufficient concentration for achieving satisfactory therapeutic value for an extended period of time.

It is another object of this invention to provide an oral sustained release pharmaceutical preparation whose residential persistence in the stomach is remarkably increased.

It is yet another object of this invention to provide an oral sustained release pharmaceutical preparation which is prepared in the form of a pilule having a specific particle size.

Another object of this invention is to provide an oral sustained release pharmaceutical preparation which can be prepared through a very simple procedure.

A further object of this invention is to provide a process for producing an oral sustained release pharmaceutical preparation.

Still another object of this invention is to provide a method of administering the drug by means of a sustained release pharmaceutical preparation.

Still another object of this invention is to provide various uses for sustained release pharmaceutical preparations.

According to the present invention, an oral sustained release pharmaceutical preparation, which comprises lower alkyl ether of cellulose, polyacrylic acid or its pharmaceutically acceptable salt, and active drugs, can be provided.

DESCRIPTION OF THE PREFERRED EMBODIMENT

The lower alkyl ether of cellulose used in the present invention results from at least partial substitution of the same or different lower alkyl ether groups for a plurality of hydroxyl groups of cellulose. The lower alkyl groups in the lower alkyl ether groups may be substituted by substituents. To speak of such substituents, a hydroxyl group, for instance, may be mentioned as a preferred example.

Examples of the optionally substituted lower alkyl groups are a methyl group and hydroxy lower alkyl groups having 3 to 8 carbon atoms.

As the lower alkyl ethers of cellulose, methyl cellulose, ethyl cellulose, hydroxyethyl cellulose, hydroxypropyl cellulose, and hydroxypropylmethyl cellulose, for instance, may be mentioned.

Of these mentioned above, hydroxypropyl cellulose are desirable ones in view of the fact that they give an excellent sustained release effect in gastric juice to the pharmaceutical preparation made therewith.

Especially, the use of hydroxypropyl cellulose is more recommendable than any other cellulose ethers. Any hydroxypropyl cellulose can be used without regard to molecular weight; however, it is preferable to use one whose 2% aqueous solution shows the viscosity ranging from 3 to 10,000 centipoises, more preferably from 1,000 to 4,000 centipoises.

As the polyacrylic acid to be used in the present invention, not only acrylic acid as a single polymer but also as a copolymer, available on the market, of acrylic acid and alkyl sucrose, methyl acrylate, methacrylic acid, methyl methacrylate, hydroxyethyl methacrylate, styrene or such vinyl ether monomer as methyl vinyl ether, whether in a single use or in a mixed use of more than one, may be mentioned.

The component mixing ratio of these copolymers may be optionally changed within such a range as to maintain water solubility or swelling property.

A mixture of polyacrylic acid and some quantity (ordinarily about 20% by weight or less) of a water soluble polymer (polymethacrylic acid or its salt, and polyethylene glycol, for instance), all available on the market, can also be used as polyacrylic acid in this invention. As pharmaceutically acceptable salt of polyacrylic acid in the present invention, its sodium salt and potassium salt are preferable ones and its degree of neutralization is optional. Polyacrylic acid or its pharmaceutically acceptable salt can be used regardless of its molecular weight; however, it is preferable to use the one whose viscosity ranges from 360 to 165,000 centipoises when it is determined at 25.0±0.5° C. on an aqueous solution (pH 7 to 7.5) of its sodium salt containing polyacrylic acid of 0.2% concentration. Polyacrylic acid or its pharmaceutically acceptable salt can be used singly or as a mixture of more than one kind in the present invention.

The mixing ratio between the lower alkyl ether of cellulose and the polyacrylic acid or its pharmencentically acceptable salt to be contained in the pharmaceutical preparation of this invention may preferably be 0.1 to 1,000 parts by weight of polyacrylic acid or its pharmaceutically acceptable salt to 10 parts by weight of lower alkyl ether of cellulose, more preferably be 0.1 to 10 parts by weight of polyacrylic acid or its pharmaceutically acceptable salt to 10 parts by weight of lower alkyl ether of cellulose.

As the original drug which is involved in this invention as its active ingredient, any drugs may be used so far as they are drugs for gastrointestinal diseases and general disease therapeutic drugs which can be expected to display much more increased therapeutic value than before as the result of a sustained release effect and the following drugs may be mentioned as such ones.

(a) Drugs for gastrointestinal diseases

Drugs for peptic ulcer such as allantoin, aldioxa, pirenzepine hydrochloride, secretin, urogastrone, cetraxate, cimetidine, ranitidine, p-(trans-4-aminomethyl cyclohexylcarbonyl) phenylpropionate hydrochlorine salt, and prostaglandins; antacids such as synthetic aluminium silicate, natural aluminium silicate, dimagnesium aluminic silicate, magnesium bismuthide aluminic silicate, dehydrated aluminum hydroxide gel, hydrotalcite, magnesium aluminic metasilicate, magnesium silicate, magnesium oxide, heavy magnesium oxide, magnesium hydroxide, magnesium carbonate, and precipitated calcium carbonate; anti-pepsin drugs such as sucrose sulfuric ester, pepstatin, and streptostatin; and digestive enzymes such as pepsin, diastase, and lipase.

(b) Drugs for central nervous system

Hypnotics and sedatives such as diazepam and estazolam; antiepileptics such as phenytoin, peprobamate, and nitrazepam; antipyretic analgesics and antiphlogistics such as acetaminophen, ethenzamide, salicylamide, pentazocine, clofezon, indometacin, ketoprofen, naproxen, flurbiprofen, dichlorophenac, clidanac, alclofenac, flufenamic acid, mefenamic acid, sulinda, piroxicam, menthol, camphor, d-penicillamine, and corticosteroide; atraxics such as chloropromazine; and anti-vertigo drugs such as isoprenaline, betahistine mesylate, and scopolamine.

(c) Antiallergic agents and antihistamic agents

Diphenhydramine, cyproheptadine, etc.

(d) Drugs for circulatory system

Cardiotonics such as digitalis and ubidecarenon; antiarrhythmic agents and β-blockers such as pindolol, propranolol hydrochloride, alprenolol hydrochloride, and oxprenolol hydrochloride; diuretics such as theophylline, trichlormethiazide, spironolactone, methyclothiazide, metolazone, tripamide, furosemide, and penflutizide; antihypertensive agents such as reserpine, clonidine methyldopa, hydralazine syrosingopine, resinnamine, cinnarizine, prazosin hydrochloride, and dihydropyridine derivatives including nifedipine; capillary stabilizers such as rutin and carbazochrome; angiotonics such as dihydroergotamine mesylate and dihydroergotoxine mesylate; coronary vasodilators such as nitroglycerin, isosorbitol dinitrate, dilazep dihydrochloride, nifedipine, diltiazem hydrochloride, trimethazidine hydrochloride, trapidil, and dipyridamole, peripheral vasodilators such as inositol and hexanicotinate; drugs for arteriosclerosis such as chlofibrate; pentoxifylline, cytochrome c, dextran sulfate sodium, pyrithioxine, citicoline, nicardipine hydrochloride, dopamine hydrochloride, prostaglandins, prostacyclins, dobutamine hydrochloride, alprostadil, and ifenprodil tartrate.

(e) Drugs for respiratory diseases

Antitussives and expectorants such as ephedrine hydrochloride, codein, and bromhexine hydrochloride; isoproterenol, dextromethorphan, ipratropium bromide, and sodium cromoglicate.

(f) Hormone drugs and hormone controling drugs

Pituary gland hormone drugs such as human growth hormone, corticotropin, oxytocin, vasopressin, and protereline tartrate; male sex hormone such as testosterone; and female sex hormone such as progesteron and estradiol.

(g) Drugs for urinary and genital organs

Uterotonics such as dinoprost and dinoprost.

(h) Metabolic drugs

Vitamins such as $1\alpha$-hydroxycholecalciferol, 1,24-dihydroxycholecalciferol, and mecobalamin; nutrients, tonics, and alteratives; glutathione, ATP, aprotinin, and gabexate mesilate.

(i) Drugs for tumor

Krestin, ancitabine hydrochloride, mitomycin C, methotrexate, carboquone, cytarabine, picibanil, 5-fluorouracil derivatives involving tegafur and carmofur.

(j) Antibiotics

Tetracycline antibiotics, penicillines, cephalosporin antibiotics, etc.

(k) Chemotherapeutic agents

Clotrimazole, pyrrolnitrin, and sulfa drugs.

Of these drugs, drugs for peptic ulcer, antacids, anitpepsin drugs, digestive enzymes, hyponotics and sedatives, antiarrhythmic agents and $\beta$-blockers, diuretics and antiotonics are preferable, and drugs for peptic ulcer, antacids, anti-pepsin drugs, digestive enzymes and anti-arrhythmic agents and $\beta$-blockers are especially preferable.

These drugs can be used singly or in a mixture of more than one provided that they are not incompatible with each other. The amount of these drugs to be used corresponds to the effective dose of the pharmaceutical preparation of this invention applied to the respective diseases and may be determined suitably depending upon the degrees of activity of the drugs, etc.

The oral sustained release pharmaceutical preparation of this invention should desirably be made to contain a foaming agent along with lower alkyl ether of cellulose and polyacrylic acid or its pharmaceutically acceptable salt. When the foaming agent is used, it gradually starts reacting with gastric juice to generate the foam of carbon dioxide in the stomach upon the oral administration of the pharmaceutical preparation thus allowing the preparation to float and prolong its staying time in the stomach, which enhances the sustained release effect of lower alkyl ether of cellulose and polyacrylic acid or its pharmaceutically acceptable salt.

As the foaming agent to be used in this invention, there are such carbonates and bicarbonates as sodium hydrogencarbonate, sodium carbonate, potassium carbonate, and potassium hydrogencarbonate. These salts may also be used in combination with an organic acid such as citric acid, tartaric acid, succinic acid, fumaric acid, maleic acid, and ascorbic acid. With the purpose of improving the foaming property and the foam-induced dispersibility of a mixture of lower alkyl ether of cellulose and polyacrylic acid or its pharmaceutically acceptable salt, or for securing the benefit of patients with anacidity, the combined use of carbonate or bicarbonate and any of such organic acids as citric acid, tartaric acid, succinic acid, fumaric acid, maleic acid, and ascorbic acid is recommendable.

The amount of the foaming agent is an important factor in the making of the present pharmaceutical preparation since it exerts influence upon the stay of the obtained preparation in the stomach and it is desirable to use the foaming agent in an amount of 10 to 50% by weight of the total weight of lower alkyl ether of cellulose and polyacrylic acid or its pharmaceutically acceptable salt. If the amount of the foaming agent exceeds 50% by weight, the preparation will starts foaming all at once in the stomach immediately after its oral administration only to make the stay short in the stomach undesirably. If the amount is less than 10% by weight, the preparation will not be able to display enough sustained releasing function in the stomach. It is especially desirable to use the foaming agent in an amount of 10 to 30% by weight of the total weight of lower alkyl ether of cellulose and polyacrylic acid or its pharmaceutically acceptable salt.

To speak of the dosage form of the oral sustained release pharmaceutical preparation of this invention, it should desirably be prepared in the form a pilule such as subtilized granule and normal granule or a tablet. It is not proper to use the pilule and tablet of excessively large size, since they are expected to disintegrate and disperse and then complete releasing the drug while they pass the site of absorption. On the other hand, it is not proper either to use the pilule and tablet of excessively small size, since the increase in their total surface area promote their integration and dispersion to allow the drug to be wholly released before passing the site of absorption thus reducing the effect of sustained release. It is, therefore, preferable to make the oral sustained release pharmaceutical preparation of this invention in the form of a pilule whose particle size ranging from 0.5 to 2 mm, especially ranging from 0.5 to 1.5 mm. As for the size of a tablet, it is preferable to form it measuring 2 to 8 mm in diameter and 1 to 5 mm in diameter and 1 to 5 mm in thickness, especially measuring 3 to 6 mm in diameter and 1 to 4 mm in thickness. The pilule or the tablet thus prepared may be used after having been filled in an ordinary hard capsule.

In order to improve the physical properties, appearance, or odor of the oral sustained release pharmaceutical preparation of this invention, it may, if desired, contain one or more than one known additive such as a lubricant, binder, and vehicle. As the lubricant, talc, stearic acid or its salt, and wax, for instance, may be mentioned. As the vehicle, there are starch, crystalline cellulose, dextrin, lactose, mannitol, and sorbitol.

The oral sustained release pharmaceutical preparation of this invention is prepared by thoroughly mixing the active drug with lower alkyl ether of cellulose and polyacrylic acid or its pharmaceutically acceptable salt, and further adding, if necessary, one or more than one forming agent, lubricant, binder, and vehicle, followed by mixing them up well to obtain a mixed compound, and then forming the compound into a pilule or a tablet, as case may require, according to a known method.

More particularly, for instance, lower alkyl ether of cellulose, polyacrylic acid or its pharmaceutically acceptable salt, and the active drug are mixed homogeneously by adding, if desired, a forming agent, lubricant, binder, etc. thereto. The mixed compound may be made into a pilule according to the dry granulating method and thus obtained pilule may further be made into a tablet according to the ordinary method. The pilule or the tablet may also be filled in a hard gelatin capsule to give hard capsules.

In cases where the active drug becomes unstable upon contact with polyacrylic acid or foaming agent, the drug may be coated with any known coating agent such as hydroxypropylmethylcellulose, polyvinyl acetal diethylaminoacetate, etc. beforehand, or may be made into minor pilules along with any known vehicle such as hydroxypropylcellulose, starch, lactose, etc. that are inert to the drug before they are formed into a pilule or a tablet of the composition provided by this invention.

The following method can also be employed as another process, in which a forming agent is used, for preparing the oral sustained release pharmaceutical preparation of this invention. Lower alkyl ether of cellulose, polyarylic acid or its pharmaceutically acceptable salt, and the active drug are first mixed homogeneously, and then, if necessary, one or more than one kind of lubricants, binders, and vehicles are added thereto and mixed thoroughly. The mixture is then subjected to dry granulating and further, if necessary, to dry classification to obtain granules of the same particle size. As for the forming agent, it is also dry granulated singly or, if desired, in combination with a lubricant, binder, and vehicle. These two kinds of granules may be mixed together and used as they are as a granule preparation or a pilule preparation, or filled in a hard capsule for convenient administration, or further made into a tablet along with a lubricant, if necessary, according to the generally practised method.

The oral sustained release pharmaceutical preparation provided by the present invention has excellent characteristics and efficacy as mentioned below.

(1) When orally administered, the oral sustained release pharmaceutical preparation absorbs the body fluid and swells, gradually releasing the drug at a controled rate. More particularly, the pharmaceutical preparation gradually starts swelling under the influence of the body fluid and the release of the drug takes place at the swollen part. The preparation can, therefore, continue to supply the site of application or the site of absorption with the drug for many ours.

(2) The sustained release pharmaceutical preparation of this invention may be regarded as a preparation endowed with an outstanding sustained release function because it is made in the form of a pilule having a specified particle size which make it possible to continue releasing the active drug in the gastro-intestinal tract for a long period of time.

(3) The pharmaceutical preparation of this invention makes it possible to easily control the rate of releasing the active drug to meet the purpose of remedial treatment by changing the volume ratio of lower alkyl ether of cellulose to polyacrylic acid or its pharmaceutically acceptable salt.

(4) Since the process of its preparation is easy and its formation is based on the press-shaping and dry slugging and granulating method, the stability of its active drug is kept undamaged and the process itself is advantageous from the economical viewpoint.

When the oral sustained release pharmaceutical preparation of this invention is produced by using a foaming agent along with lower alkyl ether of cellulose and polyacrylic acid or its pharmaceutically acceptable salt, it will become an especially excellent oral sustained release pharmaceutical preparation in the following points.

(1) It stays floating in the stomach for a long time and accordingly its active drug can be made to work in high concentration directly and locally on the affected part in the stomach without allowing itself to pass the site of absorption or the site of action before releasing the drug.

(2) Upon absorption of gastric juice, it disperses in the state of floating granules, which then swell and release the drug gradually. To explain the state in detail, it starts forming under the influence of gastric juice acidity, thus allowing the mixture of lower alkyl ether of cellulose, polyacrylic acid or its pharmaceutically acceptable salt, and the active drug to disperse in the state of floating particles. Then the dispersed particles gradually become swollen one by one. Since the release of the active drug takes place at the swollen part of the particle, it can keep supplying the drug to the diseased part or the site of absorption for many hours.

EXAMPLES

The present invention will now be further illustrated in detail by, but is by no means limited to, the following Examples, wherein "parts" are all by weight unless otherwise noted.

EXAMPLE 1

It was made apparent in the following experiment that the release of the active drug from the pharmaceutical preparation of this invention was carried out gradually.

A mixture consisting of 95 parts by weight of a mixture of hydroxypropylcellulose and polyacrylic acid mixed in an uneven ratio and 5 parts by weight of riboflavin was made into granules ranging from 12 to 24 mesh in particle size according to the dry granulating method.

Apart from the above procedure, granules ranging from 12 to 24 mesh in particle size were prepared according to the dry granulating method from a mixture comprising 70 parts by weight of a mixture of hydroxypropylcellulose and polyacrylic acid mixed in an uneven ratio, 5 parts by weight of riboflavin, and 25 parts by weight of sodium hydrogencarbonate.

Another type of granules ranging from 12 to 24 mesh in particle size were made according to the dry granulating method from a mixture of 95 parts by weight of hydroxypropylcellulose or lactose and 5 parts by weight of riboflavin.

Still another type of granules ranging from 12 to 24 mesh in particle size were made according to the dry granulating method from a mixture consisting of 70 parts by weight of hydroxypropylcellulose or lactose, 25 parts by weight of sodium hydrogencarbonate, and 5 parts by weight of riboflavin.

The riboflavin dissolution test was made according to Japanese Pharmacopoeia's dissolution test method by use of 200 mg each of the specimens in the form of granule. The dissolution test was conducted according to the second method by use of 500 ml of the first solution as the specimen solution under the condition of 100 rotations.

The result is shown in Table 1 and Table 2.

TABLE 1

| Dissolubility | Hidroxypropylcellulose*1/ polyacrylic acid*2/ sodium hydrogencarbonate | | cellulose*1/ sodium hydrogencarbonate | Lactose/ sodium hydrogencarbonate |
|---|---|---|---|---|
| | 59.5/10.5/25 | 29/21/25 | 70/25 | 70/25 |
| Time (hr) for 50% dissolution | 3.3 | 3.5 | 1.2 | 0.05 |
| Time (hr) for 80% dissolution | 7.5 | 8.0 | 2.3 | 0.15 |

*1 2% aqueous solution, viscosity of 2,080 centipoises, at 20° C.
*2 0.2% aqueous solution (pH 7.3), viscosity of 11,500 centipoises, at 25° C.

TABLE 2

| Dissolubility | Hydroxypropylcellulose*1/ polyacrylic acid*2 | | | Hydroxypropylcellulose*1 | Lactose |
|---|---|---|---|---|---|
| | 85/15 | 70/30 | 50/50 | 100 | 100 |
| Time (hr) for 50% dissolution | 2.3 | 2.4 | 1.3 | 1.2 | 0.05 |
| Time (hr) for 80% dissolution | 4.7 | 5.5 | 2.3 | 2.0 | 0.17 |

*1 2% aqueous solution, viscosity of 2,080 centipoises, at 20° C.
*2 0.2% aqueous solution (pH 7.3), viscosity of 11,500 centipoises, at 25° C.

It is apparent from Table 1 and Table 2 that the mixture of hydroxypropylcellulose and polyacrylic acid shows the sustained release and the dissolution time varies depending upon the mixing ratio. In case where the mixture contains sodium hydrogencarbonate, the granular composition dispersed and floated and the dissolution time was further extended. No floating was found with the granular composition which did not contain a foaming agent.

EXAMPLE 2

Two kinds of pharmaceutical preparations, one being the pilule preparation, ranging from 0.71 to 1.41 mm in particle size, composed of hydroxypropylcellulose containing 5% riboflavin/polyacrylic acid (weight ratio of hydroxypropylcellulose/polyacrylic acid: 70/30) prepared in Example 1 and another being a pilule preparation, ranging from 0.71 to 1.41 mm in particle size, composed of lactose containing 5% riboflavin/starch (weight ratio of lactose/starch: 70/30) used as a control, were given to 5 normal healthy persons in dose of 400 mg (cont. 20 mg of riboflavin) respectively according to the cross over test method with a 1-week suspension period between the test doses. The amount of free riboflavin evacuated in the respective urine was determined according to the fluorophotometric method to give a result as shown in Table 3.

TABLE 3

| | Human | Urinary evacuating rate (μg/hr) | | | | | | | |
|---|---|---|---|---|---|---|---|---|---|
| | | After 1 hr | After 2 hr | After 3 hr | After 4 hr | After 6 hr | After 8 hr | After 12 hr | After 24 hr |
| Pilule of hydroxypropyl cellulose/ polyacryl acid (70/30) | A | 0 | 81 | 172 | 254 | 294 | 265 | 192 | 71 |
| | B | 82 | 212 | 315 | 422 | 491 | 395 | 358 | 138 |
| | C | 28 | 130 | 204 | 301 | 352 | 348 | 287 | 117 |
| | D | 30 | 172 | 271 | 375 | 321 | 352 | 213 | 89 |
| | Average | 35.0 | 148.8 | 240.5 | 338.0 | 364.5 | 340.2 | 262.5 | 103.4 |
| Pilule of lactose/ starch (70/30) | A | 21 | 182 | 527 | 510 | 148 | 82 | 11 | — |
| | B | 17 | 385 | 902 | 732 | 338 | 243 | 108 | — |
| | C | 42 | 271 | 613 | 578 | 227 | 157 | 24 | — |
| | D | 84 | 309 | 793 | 609 | 242 | 181 | 60 | — |
| | Average | 66.0 | 286.8 | 708.8 | 607.3 | 238.8 | 165.8 | 50.8 | — |

EXAMPLE 3

85 parts by weight of hydroxypropylcellulose (viscosity of 2% aqueous solution at 20° C. being 2080 centipoises), 15 parts by weight of polyacrylic acid (viscosity of 0.2% aqueous solution of pH 7.3 at 25° C. being 11,500 centipoises), 2 parts by weight of dyestuff (amaranth), and 50 parts by weight of sodium hydrogencarbonate were mixed homogeneously. The mixture was dry granulated into granules ranging from 20 to 24 mech (0.70 mm to 0.84 mm) in particle size. 150 mg of thus prepared granule was filled in No. 2 capsule, which was then inspected with the use of Japanese Pharmacopeia's dissolution tester (No. 2 method, 1st solution 500 ml, 100 rpm). It was observed that the capsule case dissolved and disappeared in 10 minutes or so allowing the freed granules to disperse and float on the test solution. It was further confirmed that the granules kept dispersing and floating even 12 hours after that.

Of the granule prepared in the above, 10 pieces were filled in a mini-hard gelatine capsule and given to a rat. Eight hours later, the rat was subjected to laparatomy and it was confirmed that the dyestuff (amaranth) still remained there to show the long stay of the granule in the stomach.

EXAMPLE 4

A powdery mixture was prepared by evenly mixing 85 parts by weight of hydroxypropylcellulose (viscosity of 2% aqueous solution at 20° C. being 2,080 centipoises) and 15 parts by weight of polyacrylic acid (viscosity of 0.2% aqueous solution pH 7.3 at 25° C. being 11,500 centipoises). A prescribed amount of sodium hydrogencarbonate powder was added thereto and mixed thoroughly. The mixture was then dry granulated into granules ranging 12 to 24 mesh in particle size. 150 mg of thus obtained granule was filled in a hard capsule and put to Japanese Pharmacopeia's dissolution tester (No. 2 method, 1st solution 500 ml, 100 rpm) to check the dispersing and floating conditions in 4 hours. The result is shown in Table 4.

TABLE 4

| Ratio of hydroxy-propylcellulose/ polyacrylic acid (85/15) to sodium hydrogencarbonate | Result | | |
|---|---|---|---|
| | Dispersion or coagulation | Suspension or sedimentation | Time of suspension (hr) |
| 30/70 | Dispersion | Suspension | 0.5 |
| 40/60 | Dispersion | Suspension | 0.8 |
| 50/50 | Dispersion | Suspension | 2.5 |
| 60/40 | Dispersion | Suspension | 3.5 |
| 70/30 | Dispersion | Suspension | 8.0 |
| 80/20 | Dispersion | Suspension | 8.5 |
| 90/10 | Dispersion | Suspension | 7.0 |
| 100/0 | Coagulation | Sedimentation | — |

As seen from Table 4, the use (10~50%) of sodium hydrogencarbonate as the foaming agent proved effective for securing dispersion and suspension.

EXAMPLE 5

70 parts by weight of hydroxypropylcellulose (viscosity of 2% aqueous solution at 20° C. being 2,080 centipoises), 30 parts by weight of polyacrylic acid (viscosity of 0.2% aqueous solution pH 7.3 at 25° C. being 11,500 centipoises), and 2 parts by weight of dyestuff (amaranth) were mixed evenly and dry granulated into a granular substance ranging from 12 to 24 mesh (0.71 mm to 1.41 mm) in particle size (hereunder referred to as granular substance (A)).

Separately, 60 parts by weight of sodium hydrogencarbonate and 40 parts by weight of citric acid were mixed well and dry granulated into a granular substance ranging from 16 to 24 mesh (0.71 mm to 1.00 mm) in particle size (hereunder referred to as granular substance (B)).

Thereafter, 70 parts by weight of granular substance (A), 30 parts by weight of granular substance (B), and 0.5 part by weight of magnesium stearate were mixed thoroughly and made into tablets measuring 10 mm in diameter, 3 mm in thickness, and weighing 200 mg respectively.

The tablets were put to Japanese Pharmacopeia's dissolution tester in the same way as Example 4 and it was confirmed that the tablets started foaming and breaking up into granules to disperse and suspend immediately after having been thrown into the test solution and that they kept dispersing and suspending even 8 hours later.

EXAMPLE 6

80 parts by weight of methyl cellulose (viscosity of 2% aqueous solution at 20 C. being 9,500 centipoises), 20 parts by weight of polyacrylic acid (viscosity of 0.2% aqueous solution pH 7.3 at 25° C. being 11,500 centipoises), 40 parts by weight of sodium hydrogencarbonate, and 20 parts by weight of isoproterenol hydrochloride were mixed uniformly. Thereafter, 0.8 part by weight of magnesium stearate was added to the obtained mixture and then the admixture was made into tablets, each having 10 mm$\phi$ diameter and hardness of 4 to 5 kg. The tablets were pulverized into granules ranging from 12 to 24 mesh in particle size and 150 mg of the granules were filled in No. 2 capsule. The capsule was then subjected to the dissolution test according to Japanese Pharmacopeia's test method (No. 2 method, 1st solution 500 ml, 150 rpm). About 10 minutes after the capsule was put in the test solution, the capsule case dissolved and disappeared letting the granules disperse on the surface of the test solution and continued dispersing in the form of a granular particle for 12 hours. The time required for 50% dissolution was 3.2 hours and the time required for 80% dissolution was 7.8 hours, which indicates a good sustained release performance.

EXAMPLE 7

60 parts by weight of hydroxypropylmethylcellulose (viscosity of 2% aqueous solution at 20° C. being 14.3 centipoises), 40 parts by weight of polyacrylic acid (viscosity of 0.2% aqueous solution pH 7.3 at 25° C. being 11,500 centipoises), and 20 parts by weight of tetracycline hydrochloride were mixed together thoroughly and further 0.6 part by weight of magnesium stearate was added thereto. Tablets, each being a diameter of 10 mm$\phi$ and hardness of 3 to 4 kg, were made from the mixture. The tablets were then crushed by use of a muller and granular substance ranging from 12 to 24 mesh was obtained by means of a classifier (hereunder referred to as granular substance (A)). On the other hand, 70 parts by weight of sodium hydrogencarbonate and 30 parts by weight of tartaric acid were mixed thoroughly and then 0.5 part by weight of magnesium stearate was added thereto. The mixture was made into tablets having a diameter of 10 mm$\phi$ and hardness of 3 to 4 kg. Thereafter, the tablets were crushed to give granules ranging from 12 to 24 mesh after classification. (hereunder referred to as granular substance (B)). 60 parts by weight of granule substance (A), 40 parts by weight of granular substance (B), and 0.5 part by weight of magnesium stearate were mixed uniformly and 200 mg of this mixture was filled in No. 2 capsule. The capsule was then subjected to the dissolution test according to the same method as Example 4. It was observed that the liberated granules kept dispersed and floating on the surface of the test solution for as long as 8 hours, and that ti took 2.5 hours for 50% dissolution and 6.5 hours for 80% dissolution to show an excellent sustained release property.

What we claim is:

1. An oral sustained release pharmaceutical preparation comprising a lower alkyl ether of cellulose, polyacrylic acid or its pharmaceutically acceptable salt, a drug, and an effective amount of an effervescent foaming agent.

2. The oral sustained release pharmaceutical preparation according to claim 1, wherein 0.1 to 1000 parts by weight of polyacrylic acid or its pharmaceutically acceptable salt is present in relation to 10 parts by weight of the lower alkyl ether of cellulose.

3. The oral sustained release pharmaceutical preparation according to claim 1, wherein said preparation is in the form of a granular pilule, tablet, or capsule.

4. The oral sustained release pharmaceutical preparation according to claim 1, wherein the particle size of the granular pilule ranges from 0.5 mm to 2 mm.

5. The oral sustained release pharmaceutical preparation according to claim 1, wherein said drug is any of drugs for gastrointestinal diseases, drugs for the central nervous system, antiallergic agents, antihistaminic agents, drugs for the circulatory system, drugs for respiratory diseases, hormone drugs, hormone controling drugs, drugs for urinary and genital organs, metabolic drugs, drugs for tumor, antibiotics and chemotherapeutic agents.

6. The oral sustained release pharmaceutical preparation according to claim 1, wherein the foaming agent is present in an amount ranging from 10 to 50% by weight in relation to the total weight of the lower alkyl ether of cellulose and polyacrylic acid or its pharmaceutically acceptable salt.

7. The oral sustained release pharmaceutical preparation according to claim 1, wherein said foaming agnet is a carbonate, a bicarbonate, or a mixture of an organic acid and a carbonate or a bicarbonate.

8. A method of administering a drug, which method comprises orally administering a pharmaceutical preparation comprising a lower alkyl ether of cellulose, polyacrylic acid or its pharmaceutically acceptable salt, a drug and an effective amount of an effervescent foaming agent, thus allowing the pharmaceutical preparation to release the drug gradually in the stomach or the intestinal tract.

* * * * *